United States Patent
Kirby et al.

(10) Patent No.: US 10,702,237 B2
(45) Date of Patent: Jul. 7, 2020

(54) THERMOPLASTIC 3-D PHANTOM

(71) Applicant: The Regents of the University of California, Oakland, CA (US)

(72) Inventors: Neil Kirby, San Francisco, CA (US); Kamal Singhrao, San Francisco, CA (US); Jean Pouliot, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 616 days.

(21) Appl. No.: 14/873,467

(22) Filed: Oct. 2, 2015

(65) Prior Publication Data

US 2016/0089106 A1 Mar. 31, 2016

Related U.S. Application Data

(63) Continuation of application No. PCT/US2014/032705, filed on Apr. 2, 2014.

(60) Provisional application No. 61/807,638, filed on Apr. 2, 2013.

(51) Int. Cl.
*A61B 6/00* (2006.01)
*A61B 6/03* (2006.01)
*A61N 5/10* (2006.01)
*G09B 23/28* (2006.01)

(52) U.S. Cl.
CPC ............ *A61B 6/583* (2013.01); *A61B 6/032* (2013.01); *A61B 6/58* (2013.01); *A61B 6/582* (2013.01); *A61N 5/10* (2013.01); *G09B 23/286* (2013.01)

(58) Field of Classification Search
CPC ......... A61B 6/032; A61B 6/582; A61B 6/583; A61B 6/58

USPC .................................................. 378/18, 207
See application file for complete search history.

(56) References Cited

U.S. PATENT DOCUMENTS

| 4,672,649 | A |   | 6/1987  | Rutt |            |
|-----------|---|---|---------|------|------------|
| 5,242,956 | A |   | 9/1993  | Clemens et al. |  |
| 5,266,035 | A | * | 11/1993 | Olsen | G09B 23/286 |
|           |   |   |         |       | 434/267 |

(Continued)

FOREIGN PATENT DOCUMENTS

WO    WO-2012/155137 A2    11/2012

OTHER PUBLICATIONS

Barron, J. L. et al. "Performance of Optical Flow Techniques" *International Journal of Computer Vision* 12.1 (1994): 43-77.

(Continued)

*Primary Examiner* — Allen C. Ho
(74) *Attorney, Agent, or Firm* — Mintz Levin Cohn Ferris Glovsky and Popeo, P.C.

(57) ABSTRACT

There is provided a radiographic three-dimensional phantom for inter alia mimicking specific anatomical parts in a computerized tomography scan. Methods are provided for a variety of purposes including detecting a difference between a measured optical deformation of a radiographic three-dimensional phantom pair and a theoretical deformation of the radiographic three-dimensional phantom pair. These three-dimensional phantom can be divided into a plurality of portions, and non-radiopaque markers can be added to the portions. The portions of the three-dimensional phantom can be re-assembled, and images of the three-dimensional phantom can be generated and compared.

15 Claims, 8 Drawing Sheets

(56) References Cited

U.S. PATENT DOCUMENTS

| | | | | |
|---|---|---|---|---|
| 5,335,260 A | | 8/1994 | Arnold | |
| 6,315,447 B1* | | 11/2001 | Nord | A61B 6/482 378/18 |
| 6,362,471 B1* | | 3/2002 | Spitz | A61B 6/485 250/252.1 |
| 6,434,214 B1* | | 8/2002 | Kawai | A61B 6/032 378/20 |
| 6,992,280 B2* | | 1/2006 | White | A61B 6/583 250/252.1 |
| 7,157,696 B2* | | 1/2007 | White | A61B 6/583 250/252.1 |
| 7,510,325 B2* | | 3/2009 | Endo | A61B 6/032 250/252.1 |
| 7,594,753 B2* | | 9/2009 | Main | A61N 5/1048 378/207 |
| 7,667,191 B2 | | 2/2010 | Serban et al. | |
| 7,738,624 B2* | | 6/2010 | Herold | A61B 6/583 378/18 |
| 7,755,031 B2* | | 7/2010 | Jang | A61B 6/5276 250/252.1 |
| 7,780,351 B2* | | 8/2010 | Heigl | A61B 6/032 378/207 |
| 7,866,884 B2* | | 1/2011 | Seto | A61B 6/541 378/18 |
| 7,907,699 B2* | | 3/2011 | Long | A61N 5/1049 378/65 |
| 7,950,849 B2* | | 5/2011 | Claus | G06T 11/005 378/18 |
| 8,007,173 B2* | | 8/2011 | Paidi | A61B 6/584 378/207 |
| 8,043,003 B2* | | 10/2011 | Vogt | G01N 23/046 378/207 |
| 8,044,359 B2* | | 10/2011 | Simon | A61N 5/1071 250/370.07 |
| 8,075,183 B2* | | 12/2011 | Thornton | A61B 6/583 378/18 |
| 8,173,968 B1* | | 5/2012 | Nelms | A61B 6/583 250/370.07 |
| 8,186,880 B1* | | 5/2012 | Arnold | A61B 6/032 378/18 |
| 8,189,889 B2* | | 5/2012 | Pearlstein | A61B 6/583 382/128 |
| 8,243,881 B2* | | 8/2012 | Kuwabara | A61B 6/5282 378/98.4 |
| 8,308,362 B2* | | 11/2012 | Dove | A61B 6/145 378/204 |
| 8,309,910 B2* | | 11/2012 | Dutta | A61B 6/032 250/252.1 |
| 8,358,818 B2* | | 1/2013 | Miga | A61B 90/36 382/128 |
| 8,615,118 B2* | | 12/2013 | Yi | G06T 11/005 382/128 |
| 8,708,562 B1* | | 4/2014 | Nosil | A61B 6/583 378/207 |
| 8,777,485 B2* | | 7/2014 | Holt | A61B 6/03 250/252.1 |
| 8,818,058 B2* | | 8/2014 | Paul | A61B 6/032 382/100 |
| 8,888,498 B2* | | 11/2014 | Bisaillon | G09B 23/285 434/267 |
| 8,891,849 B2* | | 11/2014 | Rohler | A61B 6/032 382/132 |
| 8,895,912 B2* | | 11/2014 | Coolens | A61B 6/583 250/252.1 |
| 8,953,861 B2* | | 2/2015 | Couch | A61B 6/032 382/131 |
| 8,958,617 B2* | | 2/2015 | Couch | A61B 6/032 382/131 |
| 8,995,777 B2* | | 3/2015 | Peters | G06T 7/75 382/224 |
| 9,014,787 B2* | | 4/2015 | Stubbs | A61N 5/1049 600/426 |
| 9,020,220 B2* | | 4/2015 | Nukui | A61B 6/488 382/128 |
| 9,259,192 B2* | | 2/2016 | Ishihara | A61B 6/032 |
| 9,323,896 B2* | | 4/2016 | Fält | A61N 5/1075 |
| 9,398,889 B2* | | 7/2016 | Kirby | A61B 6/032 |
| 9,408,579 B2* | | 8/2016 | Yamakawa | A61B 6/14 |
| 9,420,986 B2* | | 8/2016 | Yamakawa | A61B 6/032 |
| 9,468,416 B2* | | 10/2016 | Liu | A61N 5/1049 |
| 9,514,658 B1* | | 12/2016 | Hart | G09B 23/30 |
| 9,524,552 B2* | | 12/2016 | Wang | A61B 6/03 |
| 9,526,471 B2* | | 12/2016 | Goodenough | A61B 6/025 |
| 9,547,893 B2* | | 1/2017 | Couch | A61B 6/032 |
| 9,610,056 B2* | | 4/2017 | Lavallee | A61B 6/032 |
| 9,668,705 B2* | | 6/2017 | Yamakawa | A61B 6/14 |
| 9,669,116 B2* | | 6/2017 | Baiu | A61K 49/0409 |
| 9,681,851 B2* | | 6/2017 | Rohler | A61B 6/032 |
| 9,750,471 B2* | | 9/2017 | Schirra | A61B 6/4241 |
| 9,861,335 B2* | | 1/2018 | Jonson | A61B 6/025 |
| 9,990,863 B2* | | 6/2018 | Chiribiri | A61B 6/583 |
| 2011/0004094 A1 | | 1/2011 | Stubbs et al. | |
| 2011/0062318 A1 | | 3/2011 | Bisaillon et al. | |

OTHER PUBLICATIONS

Horn, B. et al. "Determining Optical Flow" *Artificial Intelligence* 17.1-3 (1981): 185-203.

Lu, W. et al. "Fast free-form deformable registration via calculus of variations" Physics in Medicine and Biology 49(2004): 3067-3087.

Lucas, B. et al. "An iterative image registration technique with an application to stereo vision" *Proceedings of Imaging Understanding Workshop* (1981): 121-130.

Rogelj, P. et al. "Symmetric image registration" *Medical Image Analysis* 10 (2006): 484-493.

Thirion, J.-P. "Image matching as a diffusion process: an analogy with Maxwell's demons" *Medical Image Analysis* 2.3 (1998): 243-260.

Wang, He. et al. "Validation of an accelerated 'demons' algorithm for deformable image registration in radiation therapy" *Physics in Medicine and Biology* 50 (2005):2887-2905.

\* cited by examiner

|  | Object | kV aim [HU] | kV [HU] | MV aim [HU] | MV [HU] |
|---|---|---|---|---|---|
| Raw | SC321 | N/A | 998.3 | N/A | 1058.6 |
| Raw | SC320 | N/A | 989.2 | N/A | 1021.4 |
| Adipose | Insert | N/A | 911.8 | N/A | 971.3 |
| Adipose | SC321+0.25% URE-FIL 15 | 911.8 | 913.7 | 971.3 | 985.1 |
| Adipose | SC320+1.15% URE-FIL 15 | 911.8 | 924.8 | 971.3 | 977.5 |
| Muscle | Insert | N/A | 1043.7 | N/A | 1049 |
| Muscle | SC321+9.4% URE-FIL 7 | 1043.7 | 1042.2 | 1049 | 1066 |
| Muscle | SC320+7% URE-FIL 7 | 1043.7 | 1049.2 | 1049 | 1064.8 |

Table 1. Comparison of smooth-cast 320 and 321, along with additives, to inserts for a tissue characterization phantom. The percentages for the additives denote their fraction by weight of the total solution. The aim for the HUs are from the values of the inserts.

Figure 2A

| Object | kV [HU] | MV [HU] |
|---|---|---|
| Low density bone | 1260.9 | 1047.8 |
| High density bone | 2098.1 | 1230.9 |
| Pure EpoxAcast | 1538.0 | 1182.2 |
| EpoxAcast + 10% CaCO₃ | 1616.6 | 1188.3 |
| EpoxAcast + 20% CaCO₃ | 1789.6 | 1237.0 |
| EpoxAcast + 30% CaCO₃ | 1862.9 | 1248.8 |

Table 2. Comparison of EpoxAcast, along with various amounts of $CaCO_3$, to inserts from a tissue characterization phantom. The percentages for the additives denote their fraction by weight of the total solution.

THERMOPLASTIC 3-D PHANTOM

CROSS-REFERENCES TO RELATED APPLICATIONS

This application is a continuation of PCT Application No. PCT/US2014/032705, filed on Apr. 2, 2014, and entitled "THERMOPLASTIC 3-D PHANTOM" which claims the benefit of U.S. Provisional Application No. 61/807,638, filed on Apr. 2, 2013, and entitled "THERMOPLASTIC 3-D PHANTOM", the entirety of which are hereby incorporated by reference herein.

BACKGROUND OF THE INVENTION

Throughout the course of diagnosis and treatment of various disorders, e.g., cancer, a patient must undergo many different medical scans. Each one of these medical images possesses different information so it is advantageous to combine information from them.

The information in the scans is stored as image intensity values at three dimensional (3-D) coordinates. However, the body is not fixed in these coordinates. Differences in patient setup and body deformations make it difficult to directly relate the position of a specific point in the anatomy on one image to the next. The images can be rigidly aligned for a specific part of the anatomy, but this alignment will not be globally accurate. Deformable image registration (DIR) algorithms can be used to warp one of the images (the moving image) so that the alignment of the scans is accurate throughout the entirety of the other image (static image), meaning that the same tissue is located at the same coordinate in both images. To accomplish this, DIR finds a mapping solution that matches the features of one image to those of another. This deformable registration can then be used to transfer information. In radiation oncology, for example, when dealing with cancer recurrence, it is important to map any previously delivered radiation dose to new patient image. This will help the treatment planner spare organs and tissues that have already received a dose close to tolerance.

DIR is already used clinically and the theoretical deformations from these registrations have been shown to be drastically different from the actual deformation. Thus, errors therein could affect patient treatment. However, there currently is no clinical standard for providing quality assurance (QA) of DIR.

Currently, one method of providing QA for DIR involves the use of a phantom that represents a single two-dimensional slice of the body. Although the phantom is constructed in three dimensions, it and its deformations are symmetric with respect to the axial direction, making it function as a two-dimensional (2-D) system.

While the use of such a 2-D system has provided some insights into DIR algorithms its applicability and usefulness is limited as it is not completely compatible with DIR algorithms. Specifically, DIR algorithms are frequently customized in order to be used with the 2-D system. These customizations decrease the value of the 2-D system as it is unclear whether discrepancies between the theoretical and actual deformation are the result of the customization or the result of the algorithm. Accordingly, improved apparatuses, systems, and methods are required.

BRIEF SUMMARY OF THE INVENTION

In a first aspect, there is provided a three-dimensional phantom. The three-dimensional phantom includes a first tissue model that is sized and shaped according to a first feature of mammalian anatomy. In some embodiments, the first tissue model can be made of a first mixture including a thermoplastic that is solid at room temperature. In some embodiments, the radiodensity of the first tissue mixture mimics the radiodensity of the first feature in a CT scan. The three-dimensional phantom includes a second tissue model that is sized and shaped according to a second feature of mammalian anatomy. The second tissue model can be made of a second mixture that is solid at room temperature. In some embodiments, the radiodensity of the second mixture mimics the radiodensity of the second feature in a CT scan, and in some embodiments, the radiodensity of the first tissue model is different than the radio density of the second tissue model.

In another aspect, there is provided a method of detecting a difference between a measured optical deformation of a radiographic three-dimensional phantom pair and a theoretical deformation of the radiographic three-dimensional phantom pair. The method includes (i) comparing a first optical image of a non-deformed radiographic phantom to a second optical image of a deformed radiographic phantom thereby obtaining a measured optical deformation. The method further includes (ii) generating a first plurality of computer tomography (CT) images from the non-deformed radiographic three-dimensional phantom and a second plurality of CT images from the deformed radiographic three-dimensional phantom, which first and second plurality of CT images are taken at varying depths in both the non-deformed and the deformed radiographic three-dimensional phantoms. The method further includes (iii) performing a deformable registration method between a first CT image of the non-deformed radiographic three-dimensional phantom and a second CT image of the deformed radiographic three-dimensional phantom using a deformable registration algorithm thereby obtaining a theoretical deformation. The method further includes (iv) comparing the measured optical deformation with the theoretical deformation thereby determining a difference between the measured optical deformation and the theoretical deformation

BRIEF DESCRIPTION OF THE DRAWINGS

FIGS. 2A and 2B are tables illustrating the radiodensity of different materials for use in the three-dimensional phantom.

FIG. 3 is a close-up of one embodiment of a three-dimensional phantom.

DETAILED DESCRIPTION OF THE INVENTION

1. Definitions

Figure 1:
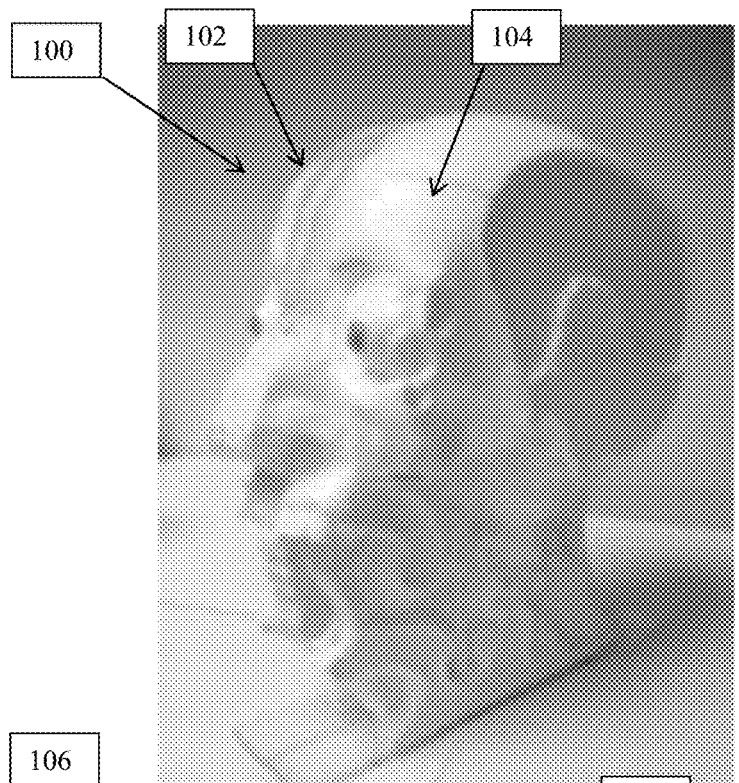
FIG. 1 is a perspective view of one embodiment of a three-dimensional phantom described herein.

An "optical image" as used herein means a digital image obtained using an optical detection device such as a digital camera.

A "computerized tomography (CT) image" as used herein means a digital image obtained using X-ray computed tomography (also referred to as Computed tomography (CT scan) or Computed axial tomography (CAT scan)).

The term "radiodensity" as used herein refer to the relative inability of electromagnetic radiation, particularly X-rays, to pass through a particular material. Though the term radiodensity is more commonly used in the context of qualitative comparison, radiodensity can also be quantified according to the Hounsfield scale, a principle which is central to X-ray computed tomography (CT scan) applications. On the Hounsfield scale, distilled water has a value of 0 Hounsfield units (HU), while air is specified as −1000 HU.

The term "kilovoltage CT scan" as used herein refers to an X-ray computed tomography scan wherein the X-rays are produced by a power source operating in excess of about 1000 V, and frequently by a power source operating in excess of about 100,000 V.

The term "megavoltage CT scan" as used herein refers to an X-ray computed tomography wherein the X-rays are produced by a power source operating in excess of about 1000 kV, and frequently by a power source operating in excess of about 6,000 kV.

The term "radiographic three-dimensional phantom" (also referred to herein as a "3-D phantom") refers to an apparatus having optically detectable non-radiopaque markers, which apparatus is sized and shaped to mimic at least a portion (e.g. substantial portion) of a mammalian anatomy component and is designed such that computerized tomography (CT) images of a plurality of planes along an axis of the 3-D phantom mimic CT images of a plurality of planes along an axis of at least a portion of a mammalian anatomy (e.g. human anatomy). The 3-D phantom and its deformations are not symmetric with respect to the axial direction, and are therefore a three-dimensional (3-D) system. In some embodiments, the outer limit of the 3-D phantom is defined at least in part by one or both of soft or hard phantom material (discussed below). As used herein, "mammalian anatomy component" refers to any anatomical structure of a mammal, and/or any percent of any anatomical structure of a mammal including, 10, 20, 30, 40, 50, 60, 70, 80, 90, or 100% of the anatomical structure or of the entire mammal. In some embodiments, the anatomical structure can be, for example, a head, brain, heart, lungs, prostate, colon, kidney, chest, torso, neck, pelvis, bladder, reproductive organ(s), abdomen, and/or extremities. The planes may be, for example, axial planes, sagittal planes, coronal planes or transversal planes.

The terms "radiographic three-dimensional phantom-pair," "pair," "3-D phantom-pair" and the like refer to radiographic three-dimensional phantoms which differ in a substantial way, e.g. by the incorporation of a deformation element in the phantom material or the deformation of one member of the radiographic three-dimensional phantom-pair. The term "deformation element" refers to a physical feature included within a 3-D phantom which serves to differentiate a non-deformed 3-D phantom from a deformed 3-D phantom. A deformation element may serve to differentiate between the members of a pair based at least in part on the shape, position or size of the deformation element in one member of the pair relative to the other member of the pair. The deformation element in one member of the pair may change the shape and position of surrounding radiographic material within 3-D phantom in one member of the pair relative to the other member of the pair. Exemplary deformation elements may include, for example, the expanded tip of a balloon catheter or an additional material inserted into the radiographic phantom (e.g., a piece of non-radiographic plastic). In one embodiment, both 3-D phantoms of a pair independently incorporate different deformation elements (e.g. of different size, shape or position). For example, the deformation element incorporated into one member of a pair is deformed to a different degree or amount relative to the deformation element incorporated into the other member of the pair. In other embodiments, only one member of a pair incorporates a deformation element.

A "non-deformed radiographic 3-D phantom" as used herein refers to one radiographic 3-D phantom of a 3-D phantom-pair, wherein the other radiographic 3-D phantom of the pair is referred to herein as a "deformed radiographic 3-D phantom". Typical deformations include, e.g., mimicking the reduction in the size of tumor during therapy and the corresponding changes in the position and size of adjacent tissue. The term "deformed radiographic 3-D phantom" refers to a radiographic 3-D phantom in which some feature (e.g., size, displacement and the like) or plurality of features of the bony phantom material and/or the soft phantom material have been deformed relative to the non-deformed radiographic 3-D phantom. Deformation can be realized by a variety of methods and can, for example, be realized by changing the temperature of the phantom material so that the phantom material becomes malleable, applying a deformative force to the phantom material, and allowing the phantom material to return to the initial temperature at which the phantom material is non-malleable and at which temperature the deformation is fixed. For example, a catheter balloon tip disposed within the soft phantom material can be inflated or deflated, thus providing a deformation. The deformation can result in, e.g., displacement of adjacent soft phantom material and/or displacement of adjacent bony phantom material. In another example, an insert (i.e., deformation element) such as an acrylic insert or non-radiopaque material insert, can be inserted into the soft phantom material to mimic the position and size of a physiological object, e.g., a tumor, within the phantom material of the deformed radiographic phantom, relative to the non-deformed radiographic phantom. The non-deformed radiographic 3-D phantom may contain no deformation element or a different deformation element (e.g. different size, shape or position).

Unless indicated otherwise, the terms "deform," "deformed," "deformation," and the like are used herein as relative terms. Therefore, in some embodiments, the non-deformed radiographic 3-D phantom does not contain a deformation element and the deformed radiographic 3-D phantom includes a deformation element. In one embodiment, the deformed radiographic 3-D phantom does not contain a deformation element and the non-deformed radiographic 3-D phantom includes a deformation element. In one embodiment the non-deformed radiographic 3-D phantom and the deformed radiographic 3-D phantom include deformation elements of substantially different size, shape and/or composition. In one embodiment neither the non-deformed radiographic 3-D phantom nor the deformed radiographic 3-D phantom include a deformation element.

A "deformable registration method" is a method in which a first CT image (commonly referred to as a "fixed" CT image) and a second CT image (commonly referred to as a "moving" CT image) are subjected to a deformable registration algorithm to obtain a warped second CT image, wherein the warped second CT image is compared with the first CT image to obtain a theoretical deformation. Accordingly, the terms "warped image," "warped CT image" "warped second CT image" and the like refer to an image obtained by subjected a moving image (i.e. the CT image that has been deformed relative to the fixed image) to a deformable registration method. In some embodiments, the deformable registration method produces a warped image based on the moving image such that the resulting warped image is more similar to the fixed image than the moving image. A variety of deformable registration methods are known and are useful in the present invention, including but not limited to the Lucas-Kanade method (Lucas, B. D., & Kanade, T., 1981, in: PROC. IMAGING UNDERSTANDING WORKSHOP (1981), pp. 121-130), the original Horn and Schunck method (Horn, B. K. P., & Schunck, B. G., 1981, Art Intell. 17:185-203), the inverse consistency Horn and Schunck method as known in the art, the iterative optical flow method (Barron, J. L., et al., 1994, Int. J. Comput. Vis. 12:43-77), the fast iterative optical flow method, the symmetric force demons method (Thirion, J. P., 1998, Med. Image Anal. 2:243-260; Rogelj, P., et al., 2006, Med. Image Anal. 10:484-493), the fast demons method (Wang, H., et al., 2005, Phys. Med. Biol. 50:2887-2905), the fast demons method with elastic regularization as known in the art, and the free-form via calculus of variations method (Lu, W. G., et al., 2004, Phys. Med. Biol. 49:3067-3087).

A "theoretical deformation" refers to a difference detected between a first position on a first CT image and the corresponding position on a warped second CT image.

The terms "deformable registration" and the like refer, as customary in the art, to a process of transforming different sets of data, e.g., computerized tomography (CT) data, into one coordinate system. Methods of deformable registration are known in the art and/or described herein.

The terms "similarity metric" and the like refer to statistical methods well known in the art of deformable registration. Exemplary similarity metrics include "CC" (cross-correlation), "MI" (mutual information), "SAD" (sum of absolute differences), "SSD" (sum of squared differences) and the like.

The terms "image similarity" and the like refer to the calculated similarity between two images, e.g., fixed and moving images, fixed and warped images, moving and warped images, and the like, as determined by methods known in the art and described herein. In one embodiment, image similarity is calculated by the sum of squared differences (SSD) similarity metric, employing equation: $SSD = \Sigma_{i=1}^{N}(W_i - F_i)^2$ (Eqn. 1). In this equation, $W_i$ and $F_i$ are the intensities of the warped and fixed images, respectively, as customarily employed in the art. Without wishing to be bound by any theory, it is believed that if a deformation algorithm focuses only on image similarity, then unphysical deformations can appear in the warped image. Accordingly, a penalty function P="similarity"+$\lambda$·"regularization" (Eqn. 2) can be employed as known in the art to reduce unphysical deformation. In Eqn. 2, "similarity" is calculated as described herein, e.g., SSD method, the "regularization" term penalizes non-smooth deformations, and the parameter "$\lambda$" is optimized to provide an optimal balance between the penalty terms. In one embodiment, the regularization term has the form of Eqn. 3;

$$R = \Sigma_i \, \Sigma_a \, \Sigma_b \left( \frac{\partial^2 \vec{D}}{\partial x_a \partial x_b} \right)^2, \quad \text{(Eqn. 3)}$$

wherein index i spans all points in the compared images, indices a and b span the three spatial coordinates of the images, and vector D is the deformation vector, as known in the art. An "image similarity value" is a numerical value for an image similarity calculation between two images.

A "measured optical deformation" refers to a difference measured between a first position of an optically detectable non-radiopaque marker(s) on a first optical image and a second position of the corresponding optically detectable non-radiopaque marker on a second optical image.

"Theoretical deformations" in the context of CT images refers to deformations predicted by a method for deformable registration.

The terms "radiographic phantom material," "phantom material" and the like refer to materials which mimic corresponding tissues, structures, and the like in a subject. Accordingly, "bony phantom material" mimics the radiographic characteristics of hard tissue, e.g., bone, enamel, cartilage and the like, and "soft phantom material" mimics the radiographic characteristics of soft tissue e.g., deformable tissue in a subject, e.g., organs, vasculature, and the like. It is understood that soft phantom material disposed within a 3-D phantom as described herein can include a plurality of distinct soft phantom material elements, e.g., soft phantom materials which mimic the radiographic characteristics of soft tissue including, for example, fat, muscle, fat-muscle intermediate, or any combination thereof. Material useful for soft phantom material includes a thermoplastic and the like, and specifically, a thermoplastic urethane and the like. Exemplary soft phantom material includes Smooth-Cast® 320 (Smooth-On, Inc. Easton, Pa.), Smooth-Cast® 321 (Smooth-On, Inc. Easton, Pa.), and the like. It is understood that the properties of soft phantom material, e.g., thermoplastic urethane, can be modulated by a variety of methods during manufacture, including e.g., addition of additives to create a mixture having a radiodensity different than the radiodensity of the thermoplastic urethane. Exemplary additives include URE-FIL® 15 (Smooth-On, Inc. Easton, Pa.), URE-FIL® 7 (Smooth-On, Inc. Easton, Pa.), brass filings, and the like. It is further understood that bony phantom material can include a plurality of distinct bony phantom material elements, e.g., bony phantom materials which mimic the radiographic characteristics of hard tissue including, for example, bone, enamel, cartilage, or any combination thereof. Material useful for bony phantom material as described herein includes a material that becomes malleable at higher temperature than the temperature at which the soft phantom material becomes malleable. In some embodiments, the bony phantom material can include a base material can be a thermoplastic including, for example, a thermoplastic urethane, and/or a resin including, for example, an epoxy resin. In some embodiments, a mixture can be formed of the base material and one or several additives including, for example, calcium carbonate. These additives can be added to the base material to create a mixture having a property different than the base material and different than the additive. In some embodiments, the additive can be added to the base material to change, for example, the radiodensity of the mixture. Specific bony phantom material includes EpoxAcast® 670HT and the like. The radiographic properties (e.g., Hounsfield units) of phantom material can be modulated by the addition of an additive also referred to herein as a radiopaque material (e.g., brass powder, and the like) during manufacture.

"Mimic" as used herein means that the aspect of a 3-D phantom, used in connection with mimic, resembles an aspect of mammalian anatomy when viewed in a CT image. In some embodiments, this resemblance can be based on size and/or shape. In some embodiments, the resemblance can be based on the relative placement of the aspect of the 3-D phantom within the 3-D phantom, the radiodensity of the aspect of the 3-D phantom, the relative radiodensity of the aspect of the 3-D phantom when compared to other aspects of the 3-D phantom (the contrast), and the like.

A "tissue model" as used herein means phantom material configured to mimic an aspect of a portion of mammalian anatomy including, for example, the size, shape, absolute radiodensity, and/or relative radiodensity of the portion of mammalian anatomy.

The term "deformable registration error metric" refers to a description, e.g., depiction, enumeration or the like, of the differences between the measured optical deformation and the theoretical deformation predicted by a method for deformable registration between a set of CT images, as described herein.

The term "radiopaque marker" refers in the customary sense to a material which can be observed in a CT scan. The term "non-radiopaque markers" refers to a material which is not substantially observed in a CT scan (e.g., the presence of the non-radiopaque marker does not substantially influence the performance of a deformable registration method or the resulting theoretical deformation). An "optically detectable non-radiopaque marker," as used herein, means a non-radiopaque marker that is detectable using a light detection device, such as an optical camera. Optically detectable non-radiopaque marker are visible when the non-deformed radiographic phantom or the deformed radiographic phantom is viewed, e.g., by an observer or an optical detection device such as a digital camera.

2. 3-D Phantom

With reference now to FIG. 1, a perspective view of one embodiment of a 3-D phantom 100 is shown. The 3-D phantom 100 can comprise a variety of shapes and sizes, and can be modeled after any desired feature of mammalian anatomy. In the embodiment depicted in FIG. 1, the 3-D phantom 100 is modeled after a human head.

In some embodiments, the 3-D phantom 100 can be divided into a plurality of portions. In some embodiments, these portions can comprise equally sized and/or similarly shaped portions of the 3-D phantom 100. In some embodiments, these portions can be divided along one or several splitting planes that can extend through the 3-D phantom 100. Advantageously, the dividing of the 3-D phantom 100 into a plurality of portions can allow the placement of non-radiopaque optical markers on an internal location of the 3-D phantom 100. This placement can advantageously allow the measurement of an actual deformation occurring at a location other than the external surface of the 3-D phantom 100.

With specific reference now to the embodiment of the 3-D phantom 100 depicted in FIG. 1, the 3-D phantom is divided into a first portion 102 and a second portion 104. As seen in FIG. 1, the first portion 102 is similarly sized and shaped to the second portion 104, and each portion approximately comprises one half of the 3-D phantom 100.

Figure 2:
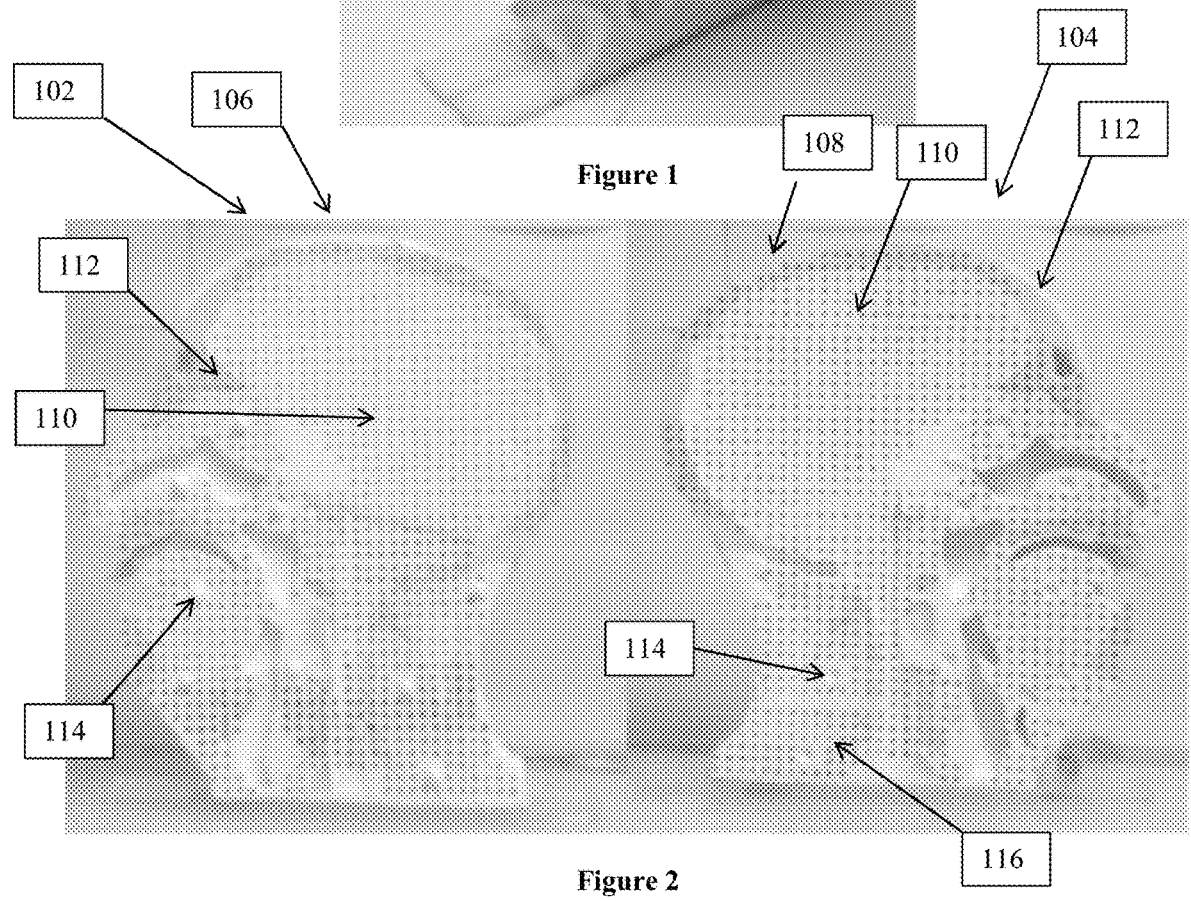
FIG. 2 is a side view of one embodiment the first and second portions of the three-dimensional Phantom.

With reference now to FIG. 2, a side view of the first portion 102 and the second portion 104 is shown. As seen in FIG. 2, the first portion 102 can comprise a first mating surface 106 and the second portion 104 can comprise a second mating surface 108. In some embodiments, the first mating surface 106 and the second mating surface 108 can be configured to abut with each other so as to form the 3-D phantom 100. In some embodiments, the first mating surface 106 and the second mating surface 108 can comprise planar and/or nonplanar surfaces. In some embodiments, for example, the first mating surface 106 and the second mating surface 108 can extend completely through the 3-D phantom 100 and/or extend less than completely through the 3-D phantom 100.

As seen in FIG. 2, the 3-D phantom 100 can comprise a variety of anatomically sized and shaped features. As specifically shown in the embodiment depicted in FIG. 2, the 3-D phantom 100 can comprise a first tissue model 110 that can be, for example, sized and shaped according to a first feature of mammalian anatomy. In some embodiments, the first tissue model 110 can comprise a phantom material, and can include, for example, a soft phantom material including, for example, a thermoplastic such as a thermoplastic urethane. In the embodiment depicted in FIG. 2, the first tissue model 110 can simulate, for example, the brain, the tongue, and/or other soft portions of the neck of a human.

The 3-D phantom 100 can further comprise a second tissue model 112 that can be, for example, sized and shaped according to a second feature of mammalian anatomy. In some embodiments, this tissue model can comprise a phantom material and can include, for example, a soft phantom material including a thermoplastic such thermoplastic urethane and/or a hard phantom material including a resin such as, for example, an epoxy resin. In the embodiment depicted in FIG. 2, the second tissue model 112 can simulate, for example, the skull, the jaw, the teeth, and the vertebrae of a human.

In some embodiments, the phantom material of the first and second tissue models 110, 112 can comprise a mixture of one or several components, which combination of components results in a desired radiodensity of the mixture. In some embodiments, this radiodensity may differ from the thermoplastic and/or resin used in the phantom material. In some embodiments, one or several additives can be added to the thermoplastic and/or resin in order to achieve a desired radiodensity and/or other desired material property. In one embodiment, for example, this desired radiodensity can be based on the actual radiodensity of the feature of mammalian anatomy that is simulated by the 3-D phantom and/or by the tissue model, and in some embodiments, the desired radiodensity can be selected so as to achieve a desired result which can include, for example, achieving a desired level of contrast between the first and second tissue models 110, 112, or any other features of the 3-D phantom 100.

In some embodiments, for example, the radiodensity of the tissue model 110, 112 can vary based on the details of the CT scan being performed on the 3-D phantom 100. Thus, for example, the radiodensity of the tissue model 110, 112 is different when a kilovoltage CT scan is being performed then when a megavoltage CT scan is performed. In some embodiments, the 3-D phantom 100 and/or the tissue models 110, 112 of the 3-D phantom 100 are configured so that the radiodensity of the tissue models 110, 112 achieves the desired radiodensity when one and/or both of the kilovoltage CT scan and a megavoltage CT scan is performed.

In some embodiments, the composition of the mixture of the tissue models 110, 112 can be specific so as to achieve the desired radiodensity when measured with either or both of the kilovoltage CT scan and a megavoltage scan. Advantageously, different additives differently impact the radiodensity of the tissue models 110, 112 in a kilovoltage CT scan as compared to a megavoltage scan. Using this disparate impact of additives on the radiodensity of the tissue models 110, 112, the radiodensity of the tissue models 110, 112 can be tailored, in some embodiments, to a desired radiodensity for both kilovoltage CT scans and/or megavoltage CT scans.

Tables 1 and 2 depict mixture compositions and their resulting radiodensity as measured in Hounsfield units (HU). In the context of Tables 1 and 2, distilled water has a value of 1000 Hounsfield units (HU), while air is specified as 0 HU. Specifically, Table 1 lists a plurality of objects, a target radiodensity measured both with a kilovoltage CT scan and a megavoltage CT scan, as well as the actual radiodensity of the object measured with both a kilovoltage CT scan and a megavoltage CT scan. As seen in Table 1, the radiodensity of Smooth-Cast® 320 and Smooth-Cast® 321 is different than the radiodensity of the insert. As also seen in Table 1, the addition of an additive to the Smooth-Cast® (SC320, SC321) creates a mixture having properties more closely matched to the radiodensity of the insert than the pure Smooth-Cast® Thus, Table 1 displays the use of an additive URE-FIL® 15 to decrease the radiodensity of the Smooth-Cast® to thereby simulate adipose tissue and the use of the additive URE-FIL® 7 to increase the radiodensity of the smooth cast to thereby simulate muscle.

Like Table 1, Table 2 lists a plurality of objects and the radiodensity of those objects measured with both a kilovoltage CT scan and a megavoltage CT scan. Specifically, Table 2 depicts a comparison of the radiodensity of pure EpoxAcast® as well as of mixtures including EpoxAcast® and some amount of calcium carbonate. The percentages of the additive shown in Table 2 denote their weight fraction of the total solution. As seen in FIG. 2, the addition of one or several additives, and specifically, the addition of calcium carbonate to a resin such as, for example, an epoxy resin including EpoxAcast® can more closely match the radiodensity of the mixture to the radiodensity of a feature of mammalian anatomy.

Referring again to FIG. 2, both the first and second portions 102, 104 include a plurality of keys 114. In some embodiments, the plurality of keys 114 can be configured to interact with each other so as to fix the position of the mating surfaces 106, 108 relative to each other, and specifically to fix the mating surfaces 106, 108 such that any deformation of one or both of the mating surfaces 106, 108 in the plane of the first mating surface 106 and/or second mating surface 108 is transferred between portions 102, 104 of the 3-D phantom 100. In the embodiment depicted in FIG. 2, the plurality of keys 114 can comprise one or several male keys and one or several female keys. In some embodiments, the male keys can be configured to engage with the female keys to thereby secure and/or fixed the first mating surface 106 to the second mating surface 108. In some embodiments, the plurality of keys 114 can comprise one or several protrusions and one or several matched depressions configured to receive the protrusions.

As seen in FIG. 2, the 3-D phantom 100 can comprise a plurality of non-radiopaque optical markers 116, also referred to herein as landmarks. In some embodiments, for example, the plurality of non-radiopaque optical markers 116 can be located on a surface of the 3-D phantom 100 including, for example, on the first and second mating surfaces 106, 108 of the first and second portions 102, 104 respectively. In some embodiments, the plurality of non-radiopaque optical markers 116 can be arranged on the surface of the 3-D phantom 100 according to a pattern and/or in a random manner. In some embodiments, for example, the markers 116 can be arranged on a surface of 3-D phantom 100 such as, for example, the first and second mating surfaces 106, 108, in a grid pattern having a marker disposed every 1 mm, 2 mm, 3 mm, 4 mm, 5 mm, 6 mm, 7 mm, 8 mm, 9 mm, 10 mm, or even greater spacing, in orthogonal (e.g., x and y) directions. In one embodiment, optically detectable non-radiopaque markers are provided in a pattern with a density of about 1-100 per square cm, 1-90 per square cm, 1-80 per square cm, 1-70 per square cm, 1-60 per square cm, 1-50 per square cm, 1-40 per square cm, 1-30 per square cm, 1-20 per square cm, 1-10 per square cm, 1-9 per square cm, 1-8 per square cm, 1-7 per square cm, 1-6 per square cm, 1-5 per square cm, 1-4 per square cm, 1-3 per square cm, 1-2 per square cm, or even 1 per square cm. Absent express indication otherwise, the term "about" in the context of a numeric value represents the nominal value ±10%. In some related embodiments, the optically detectable non-radiopaque markers are space evenly (e.g. in even orthogonal directions) where a density is provided.

Figures 2B, 3:
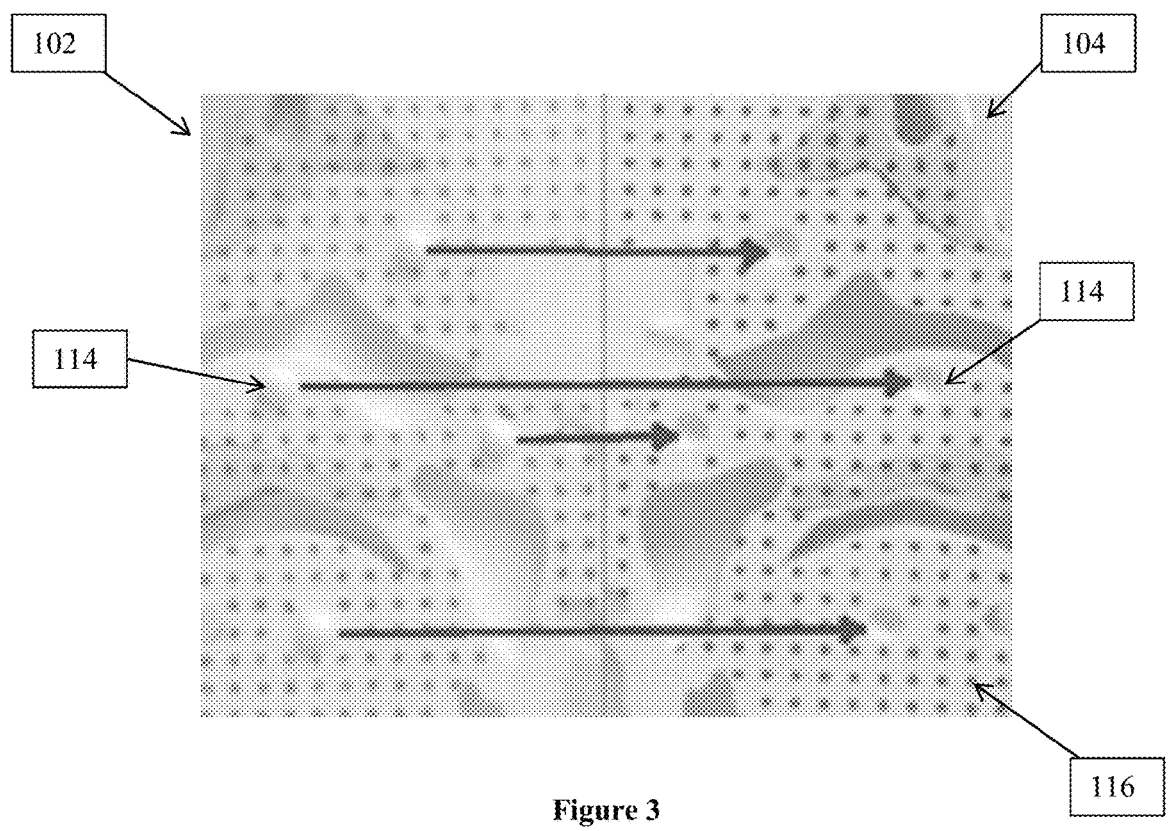

FIG. 3 is a close-up of a piece of both the first portion 102 and a second portion 104 that more clearly depicts the plurality of keys 114 and the plurality of non-radiopaque optical markers 116. As seen in FIG. 3, and as indicated by an arrow between the plurality of keys 114, the plurality of keys 114 correspond with each other to thereby fix the relative position of the first portion 102 and the second portion 104.

Figure 4:
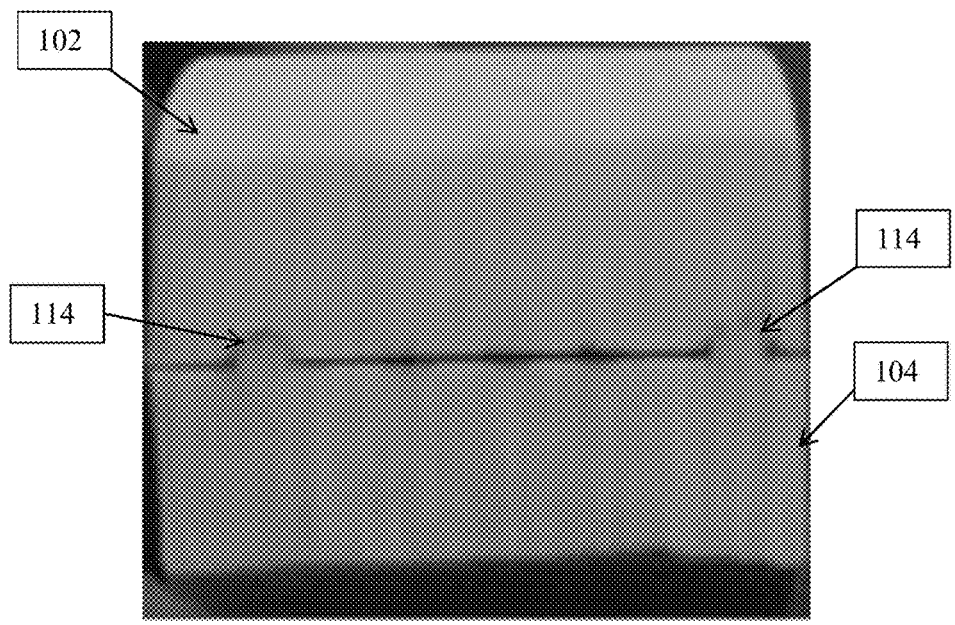
FIG. 4 is a perspective view showing the interaction of keys of the three-dimensional phantom.

With reference now to FIG. 4, a perspective view of one embodiment of the interaction of the plurality of keys 114 in fixing the relative position of the first portion 102 and the second portion 104 is shown. As seen in FIG. 4, the plurality of keys 114 comprise a matched pair of a depression and a protrusion, which protrusion penetrates the depression to thereby prevent movement of the first and second portions 102, 104 in a direction parallel to the mating surfaces 106, 108 of the first and second portions 102, 104. A person of skill in the art will recognize that wide variety of plurality of keys 114 in key shapes can be used in securing the first and second portions 102, 104, and that the present disclosure is not limited to the specific embodiment depicted in FIG. 4.

In some embodiments, the 3-D phantom 100 can further comprise a force member (not shown). In some embodiments, the force member can comprise any feature configured to apply a force to the first and second portions 102, 104 so as to bring the first and second mating surfaces 106, 108 of the first and second portions 102, 104 into intimate contact and to eliminate any spaces between the first and second mating surfaces 106, 108. In some embodiments, this force member can comprise, for example, a clamp, a rubber band, and/or any other feature capable of developing the desired force.

3. Methods

In a first aspect, there is provided a method of detecting a difference a measured optical deformation of a radiographic three-dimensional phantom pair and a theoretical deformation of the radiographic three-dimensional phantom pair. The method includes (i) comparing a first optical image of a non-deformed radiographic three-dimensional phantom to a second optical image of a deformed radiographic three-dimensional phantom thereby obtaining a measured optical deformation. The method further includes (ii) generating a first plurality of computer tomography (CT) images from the non-deformed radiographic three-dimensional phantom and a second plurality of CT images from the deformed radiographic three-dimensional phantom, wherein the first and second plurality of CT images are taken at varying depths in both the non-deformed and the deformed radiographic three-dimensional phantoms. The method further includes (iii) performing a deformable registration method between the first plurality of CT images and the second plurality of CT images using a deformable registration algorithm thereby obtaining a theoretical deformation. The method further includes (iv) comparing the measured optical deformation with the theoretical deformation thereby determining a difference between the measured optical deformation and the theoretical deformation.

In one embodiment, there is provided a method of detecting a difference between a measured optical deformation of a radiographic 3-D phantom pair and a theoretical deformation of the radiographic 3-D phantom pair. The method includes: (a) receiving a first optical image of a non-deformed radiographic 3-D phantom and a second optical image of a deformed radiographic 3-D phantom at a system processor. The method further includes: (b) calculating a comparison of the first optical image of the non-deformed radiographic 3-D phantom with the second optical image of the deformed radiographic 3-D phantom at the system processor, hereby obtaining a measured optical deformation. The method further includes: (c) generating a first plurality of scan images of the non-deformed radiographic three-dimensional phantom and a second plurality of CT images from the deformed radiographic three-dimensional phantom, which pluralities of CT images are taken at varying depths in both the non-deformed and the deformed radiographic three-dimensional phantoms. The method further includes: (d) performing a deformable registration method between the first plurality of CT images of the non-deformed radiographic 3-D phantom and the second plurality of CT images of the deformed radiographic 3-D phantom using a deformable registration algorithm thereby obtaining a theoretical deformation. The method further includes (e) calculating a comparison of the measured optical deformation with the theoretical deformation at the system processor, thereby determining a difference between the measured optical deformation and the theoretical deformation.

In one embodiment, the system processor is, e.g., a desktop computer, workstation, laptop computer, or other computer platform with sufficient resources to perform the processing functions described herein. In one embodiment, the system processor includes hardware elements that can be electrically coupled via a bus (or may otherwise be in communication, as appropriate). The hardware elements can include one or more central processor units (CPUs), including without limitation one or more general-purpose processors and/or one or more special-purpose processors or processor cores. The hardware elements can further include one or more input devices, such as a computer mouse, a keyboard, a touchpad, and/or the like for providing user input; and one or more output devices, such as a flat panel display device, a printer, visual projection unit, and/or the like. The system processor may further include (and/or be in communication with) one or more storage devices, which can include, without limitation, local and/or network accessible storage and/or can include, without limitation, a disk drive, a drive array, an optical storage device, solid-state storage device such as a random access memory ("RAM"), and/or a read-only memory ("ROM"), which can be programmable, flash-updateable, and/or the like.

Further to any embodiment described above, in one embodiment the first optical image and the second optical image are obtained prior to step (i). In one embodiment, the first optical image and the second optical image are obtained prior to step (a).

Further to any embodiment described above, in one embodiment the non-deformed radiographic 3-D phantom and the deformed radiographic 3-D phantom are constructed prior to step (i). In one embodiment the non-deformed radiographic 3-D phantom and the deformed radiographic 3-D phantom are constructed prior to step (a).

Further to any embodiment described above, in one embodiment, the non-deformed radiographic 3-D phantom and the deformed radiographic 3-D phantom can include any of the features of the 3-D phantom discussed in greater detail throughout this application.

In another aspect, there is provided a method for verifying and/or adjusting a DIR algorithms with a 3-D phantom 100. This method includes selecting and/or constructing a 3-D phantom 100. In some embodiments, this 3-D phantom 100 can correspond to aspects of mammalian anatomy that will be CT imaged. Thus, in one embodiment in which a human head will be CT image, the 3-D phantom 100 can comprise a human head shaped 3-D phantom 100 that can include one or several anatomical features in the head including, for example, a nasal passageway, sinus cavity, time, mouth, teeth, char, or any other desired in the future. In some embodiments, the 3-D phantom 100 can be constructed to include some or all the features discussed at greater length above. In some embodiments, the selecting and/or constructing a 3-D phantom 100 can include selecting and/or constructing the 3-D phantom pair including both a non-deformed 3-D phantom and a deformed 3-D phantom. In some embodiments, for example, a non-deformed 3-D phantom can be made into a deformed 3-D phantom by heating the non-deformed 3-D phantom to a temperature at which some or all of the phantom material of the non-deformed 3-D phantom is malleable. A force can then be applied to the 3-D phantom which force can deform some or all of the 3-D phantom. This force and the resulting deformation is maintained until the phantom material cools thereby fixing the deformation into the 3-D phantom 100.

The method for verifying and/or adjusting a DIR algorithm with the 3-D phantom 100 further includes generating an optical image of the non-deformed 3-D phantom, an optical image of the deformed 3-D phantom, a plurality of CT images of the non-deformed 3-D phantom, and a plurality of CT images of the deformed 3-D phantom. In some embodiments, the optical images of the 3-D phantoms 100 can allow the identification of one or several non-radiopaque optical markers 116 located on the 3-D phantom 100 and thereby allow the measurement of the deformation between the non-deformed 3-D phantom and the deformed 3-D phantom. In some embodiments, the plurality of CT images of the deformed 3-D phantom and of the non-deformed 3-D phantom can be taken at a variety of depths within the 3-D phantoms 100. In some embodiments, the image planes of the plurality of CT images of the non-deformed 3-D phantom can be parallel in the image planes of the plurality of CT images of the deformed 3-D phantom can be parallel.

After the optical and CT images have been captured, these images can be used to measure the actual deformation of the 3-D phantom and to calculate the theoretical deformation of the 3-D phantom. This calculation can be performed at the system processor in accordance to stored instructions. In some embodiments, for example, the measurement of the actual deformation can include measuring the displacement of one or several of the non-radiopaque optical markers 116. In some embodiments, this displacement can be measured within the plane in which the non-radiopaque optical markers 116 is located (2-D measurement), and in some embodiments, this displacement can be measured both within the plane which the non-radiopaque optical marker 116 is located as well as displacements out of the plane in which the non-radiopaque optical markers 116 are located (3-D measurement).

Figure 5:
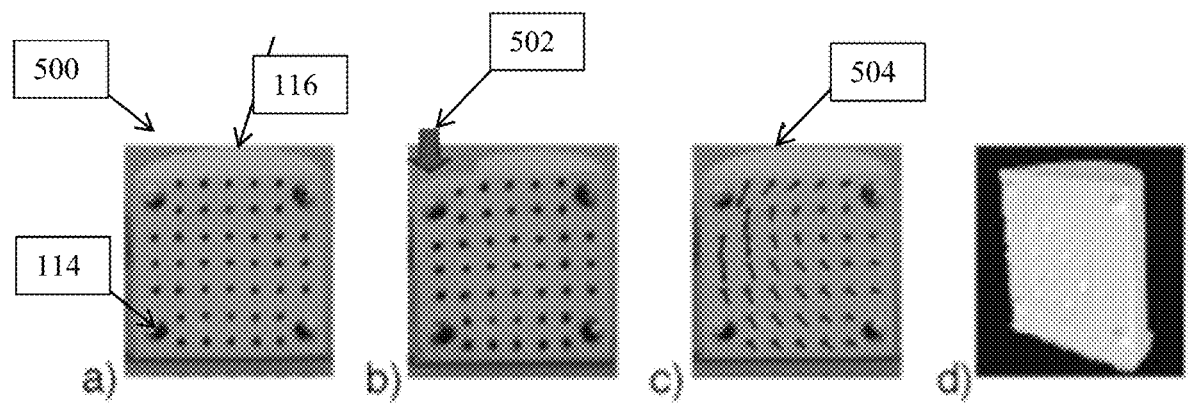
FIG. 5 depicts a process for measuring the deformation of a three-dimensional phantom.

FIG. 5 depicts one embodiment in which the deformation is measured. FIG. 5 depicts one embodiment of one half of a scaled down prostate 3-D phantom 500 both before deformation (a) and after deformation (b). As seen in FIG. 5(a), the 3-D phantom includes a plurality of keys 114 and a plurality of non-radiopaque optical markers 116. Referring now to FIG. 5 (b), the 3-D phantom is deformed by the application of the force indicated by the arrow 502. In some embodiments, this step can include changing the temperature the 3-D phantom so that the phantom material of the 3-D phantom 500 is malleable. After the force 502 has been applied, the temperature of the 3-D phantom 500 can be again changed so that the phantom material is no longer malleable and the deformation is fixed in the 3-D phantom 500. In some embodiments, the distance of the displacement between the non-radiopaque optical markers 116 can be measured using the optical images of both the non-deformed 3-D phantom and the deformed 3-D phantom.

In some embodiments, these displacements of the non-radiopaque optical markers 116 can be, for example, within the plane in which the non-radiopaque optical markers 116 are located. FIG. 5 (c) illustrates a deformation field 504 overlaying the 3-D phantom 500. The deformation field 500 indicates the direction and displacement of each of the non-radiopaque markers 116.

In some embodiments, the portion of the 3-D phantom 100 containing the non-radiopaque optical markers 116 can be scanned to determine the displacement of the non-radiopaque optical markers 116 out of the plane in which the markers are located. In some embodiments, this scan can be performed using a laser and/or a surface contouring technique such as can be performed with a CT scanner.

After the actual and the theoretical deformation of the 3-D phantom 100 has been measured and/or calculated, the actual and the theoretical deformation can be compared and a similarity metric can be calculated. In some embodiments, the similarity metric can be calculated by the system processor. In some embodiments, the similarity metric can be used to calculated image error indicative of the inaccuracies of the theoretical deformation. In some embodiments, the similarity metric and/or the image error can be used to adjust the DIR algorithm so as to maximize similarity metric and/or minimize the image error. In some embodiments, the adjustment to the DIR algorithm can include changing the number of iterations performed by the algorithm, changing the step size of the algorithm, changing the number of control points, and/or changing the amount of smoothing performed by the algorithm.

After the DIR algorithm has been adjusted, new CT images can be collected of both the non-deformed and the deformed 3-D phantom and the process can be repeated to validate the accuracy of the DIR algorithm.

Figure 6:
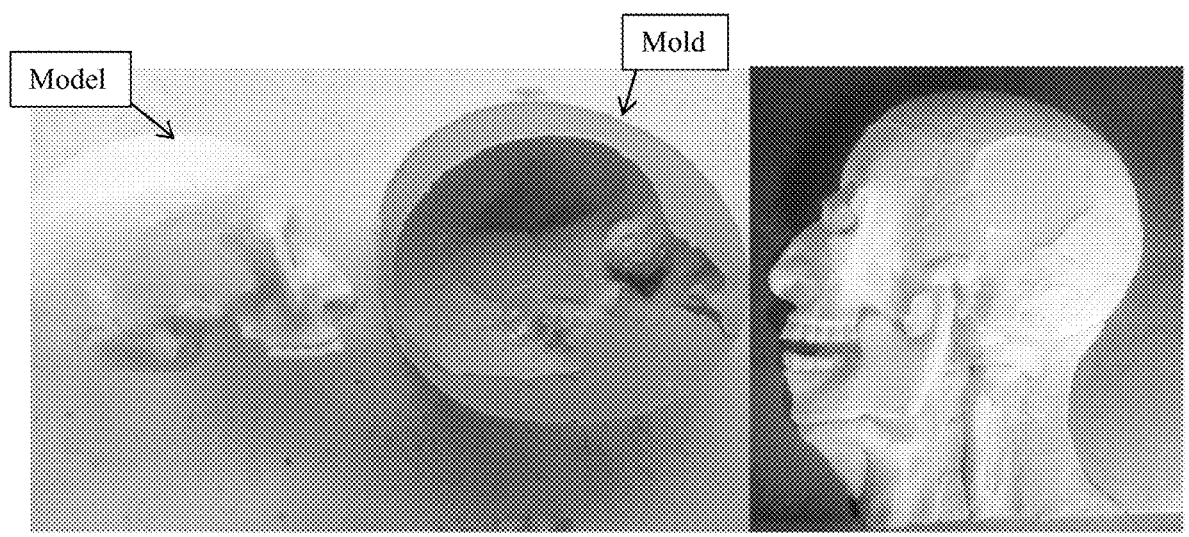
FIG. 6 is a side view of a model and a mold for three-dimensional phantom.
Figure 7:
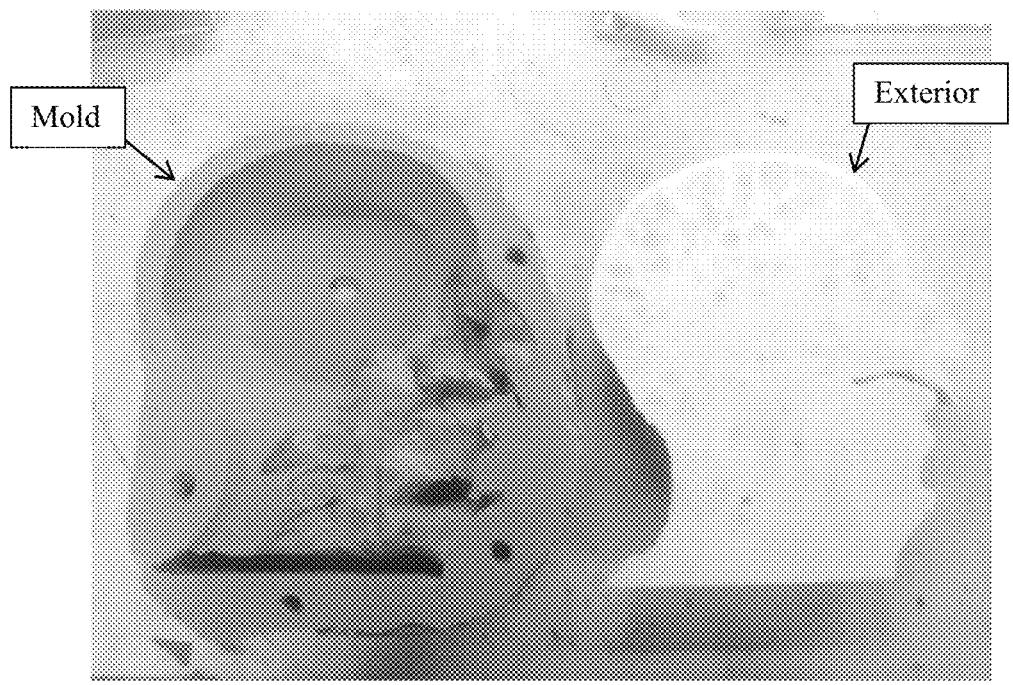
FIG. 7 is a side view of a mold for three-dimensional phantom an exterior of the three-dimensional phantom
Figure 8:
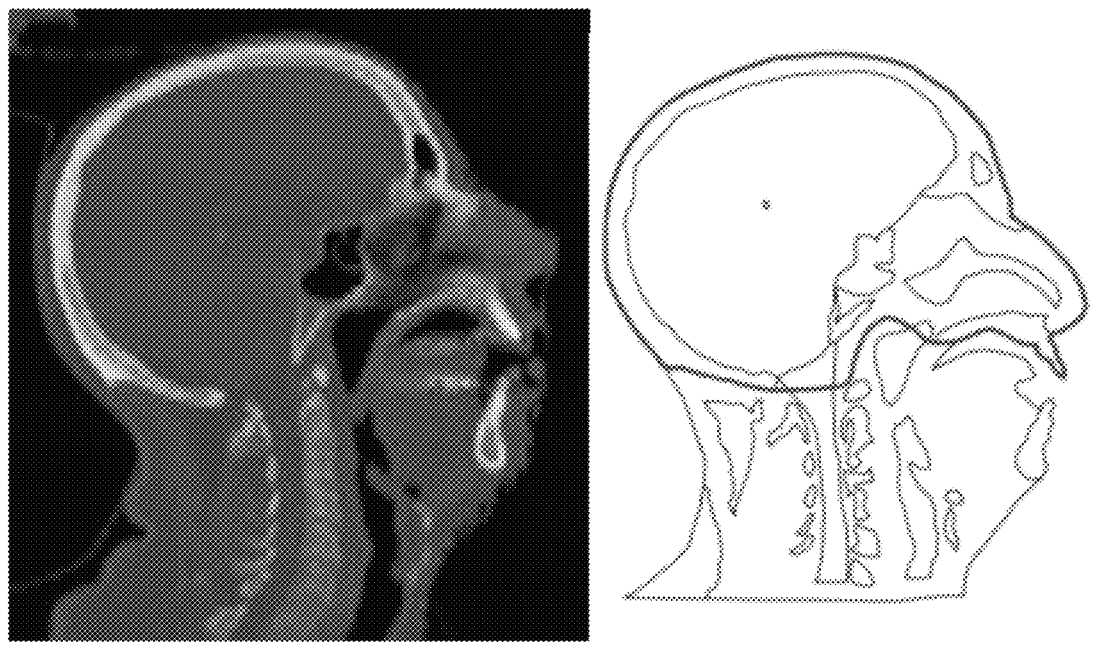
FIG. 8 depicts a CT image and an outline of the anatomy generated from CT image.
Figure 9:
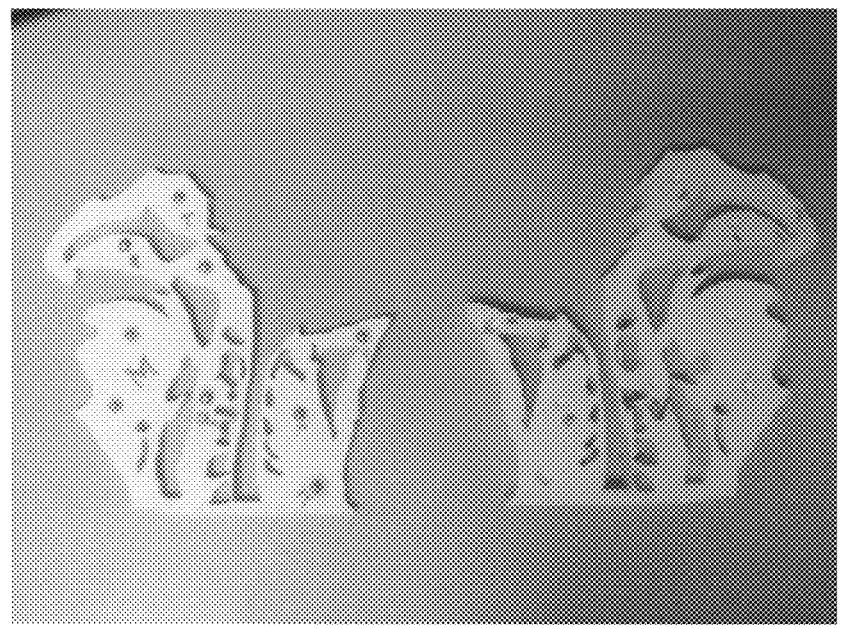
FIG. 9 is a side view of anatomically correct pieces that can be used in connection with the exterior of the 3-D phantom.
Figure 10:
FIG. 10 is a perspective view of anatomically correct pieces overlaid on a portion of the exterior of the three-dimensional phantom.

In another aspect, there is provided a method for creating a 3-D phantom 100. This method is depicted in FIGS. 6 to 11. The method includes building a model for the exterior of the 3-D phantom. In one embodiment, this model for the exterior of the 3-D phantom can define the outer bounds of the 3-D phantom. The specific embodiment depicted in FIG. 6, the exterior of the 3-D phantom is built by the addition of the material such as clay to a model of a skull. The model of the exterior of the 3-D phantom can be used to create a mold. As seen in FIG. 6, the mold can be used to cast an exterior of the 3-D phantom, and in some embodiments, the exterior of the 3-D phantom can be cast from thermoplastic urethane.

The method further includes collecting an image such as, for example, CT image of an aspect of mammalian anatomy corresponding to the exterior of the 3-D phantom. In the embodiment depicted in FIG. 6 through 11, a CT image of a head is collected, which image is used to create additional portions of the 3-D phantom. In some embodiments, for example, a mold of the additional portions for use in the 3-D phantom can be created. Specifically, in one embodiment, a model is created and is used to create a mold, and specifically, a model can be created from acrylic, which acrylic shaped to the desired size and/or shape by, for example, laser cutting, and can be used to form a mold. The desired portions for use with the 3-D phantom can be cast in the mold and can be cast from materials including, for example, a thermoplastic urethane and/or a resin including epoxy resin. In some embodiments, the portions of the 3-D phantom can be configured to include keys, and in one embodiment, for example, a plurality of paired semi-spherical holes are drilled into the cast portions for use with the 3-D phantom and key objects such as, for example, ball bearings are secured into one of the paired semi-spherical holes.

Figure 11:
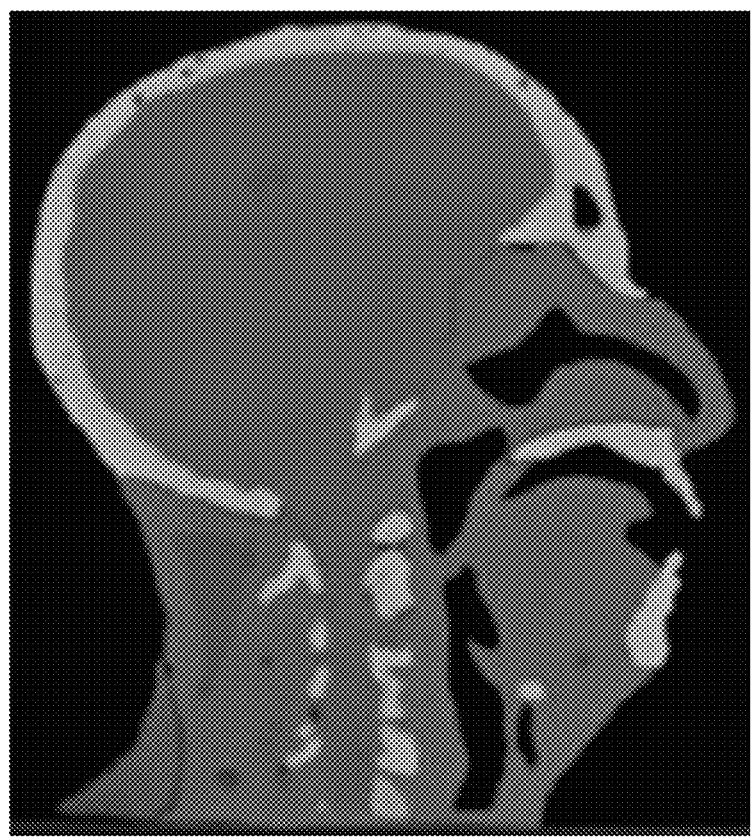
FIG. 11 depicts CT image of one embodiment of the three-dimensional phantom.

After the portions for use with the 3-D phantom have been prepared, they can be secured to the exterior of the 3-D phantom. In some embodiments, for example, these portions can be glued onto the exterior portion of the 3-D phantom, thereby forming the 3-D phantom model which can then, for example be cast into a mold which mold can be used for casting other 3-D phantoms. FIG. 11 depicts a CT image of one embodiment of a 3-D phantom created as outlined above.

Further to any of the methods or devices described herein, in some embodiments two separate radiographic phantoms are employed, i.e., a "3-D phantom-pair," wherein the only substantive difference, in the context of an optical or CT image, between the members of the pair is a deformation. The term "substantive difference" in this context means that the members of the 3-D phantom-pair differ only in the deformation and the effects thereof (e.g., displacement of tissue adjacent to the deformation). In some embodiments, a single radiographic 3-D phantom is employed, which single radiographic 3-D phantom can undergo deformation in order to model a corresponding deformation observed in a subject, e.g., growth or reduction of a tumor, inflation or deflation of a bladder or other cavity, and the like.

Accordingly, in some embodiments, the non-deformed radiographic phantom and the deformed radiographic phantom are distinct devices having substantially identical placements of the bony phantom material, substantially identical amounts of the soft phantom material, and substantially identical placement of surface markers.

The above description of embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated. Thus, it will be appreciated that the invention is intended to cover all modifications and equivalents within the scope of the following claims.

What is claimed is:

1. A three-dimensional phantom comprising:
    a first tissue model sized and shaped according to a first feature of mammalian anatomy, the first tissue model comprising a first mixture comprising a thermoplastic that is solid at room temperature, wherein a radiodensity of said first mixture mimics a radiodensity of said first feature in a CT scan; and
    a second tissue model sized and shaped according to a second feature of mammalian anatomy, the second tissue model comprising a second mixture that is solid at room temperature, wherein a radiodensity of said second mixture mimics a radiodensity of said second feature in a CT scan;
    a first portion comprising a first mating surface, wherein the first mating surface comprises a plurality of first keys and a plurality of first optically detectable non-radiopaque markers; and
    a second portion comprising a second mating surface configured to mate with the first mating surface, wherein the second mating surface comprises a plurality of second keys and a plurality of second optically detectable non-radiopaque markers, wherein the plurality of second keys engage with the plurality of first keys to prevent movement of the first portion relative to the second portion and parallel to the first mating surface and the second mating surface;
    wherein the radiodensity of the first mixture is different than the radiodensity of the second mixture.

2. The three-dimensional phantom of claim 1, wherein the radiodensity of the first mixture mimics the radiodensity of said first feature in a kilovoltage computed tomography scan.

3. The three-dimensional phantom of claim 1, wherein the radiodensity of the first mixture mimics the radiodensity of said first feature in a megavoltage computed tomography scan.

4. The three-dimensional phantom of claim 1, wherein the radiodensity of the first mixture mimics the radiodensity of said first feature in both a megavoltage computed tomography scan and a kilovoltage computed tomography scan.

5. The three-dimensional phantom of claim 1, wherein the second tissue model is configured to represent a hard tissue.

6. The three-dimensional phantom of claim 5, wherein the second mixture comprises a resin and an additive.

7. The three-dimensional phantom of claim 6, wherein the resin comprises an epoxy resin and the additive comprise calcium carbonate.

8. The three-dimensional phantom of claim 1, wherein at least one of the plurality of first optically detectable non-radiopaque markers and the plurality of second optically detectable non-radiopaque markers are arranged in a pattern.

9. The three-dimensional phantom of claim 8, wherein the pattern comprises a grid.

10. The three-dimensional phantom of claim 1, wherein the plurality of first keys comprise a plurality of protrusions, and the plurality of second keys comprise a plurality of depressions sized to receive the plurality of protrusions.

11. A three-dimensional phantom comprising:
    a first tissue model sized and shaped according to a first feature of mammalian anatomy, the first tissue model comprising a first mixture comprising a thermoplastic that is solid at room temperature, wherein a radiodensity of said first mixture mimics a radiodensity of said first feature in a CT scan; and
    a second tissue model sized and shaped according to a second feature of mammalian anatomy, the second tissue model comprising a second mixture that is solid at room temperature, wherein a radiodensity of said second mixture mimics a radiodensity of said second feature in a CT scan, wherein the second tissue model is configured to represent a hard tissue and wherein the second mixture comprises a resin and an additive;
    wherein the radiodensity of the first mixture is different than the radiodensity of the second mixture.

12. A method of detecting a difference between a measured optical deformation of a radiographic three-dimensional phantom pair and a theoretical deformation of said radiographic three-dimensional phantom pair, said method comprising:
    (i) comparing a first optical image of a non-deformed radiographic three-dimensional phantom to a second optical image of a deformed radiographic three-dimensional phantom thereby obtaining a measured optical deformation;
    (ii) generating a first plurality of computed tomography (CT) images from said non-deformed radiographic three-dimensional phantom and a second plurality of CT images from said deformed radiographic three-dimensional phantom, wherein the first plurality of CT images and the second plurality of CT images are taken at varying depths in both the non-deformed radiographic three-dimensional phantom and the deformed radiographic three-dimensional phantom;
    (iii) performing a deformable registration method between the first plurality of CT images and the second plurality of CT images using a deformable registration algorithm thereby obtaining a theoretical deformation; and
    (iv) comparing said measured optical deformation with said theoretical deformation thereby determining a difference between said measured optical deformation and said theoretical deformation.

13. The method of claim 12, further comprising, prior to step (i), obtaining said first optical image and said second optical image.

14. The method of claim 12, further comprising, prior to step (i), constructing said non-deformed radiographic three-dimensional phantom and said deformed radiographic three-dimensional phantom.

15. The method of claim 12, wherein the non-deformed radiographic three-dimensional phantom and the deformed radiographic three-dimensional phantom comprise the three-dimensional phantom described in claim 1 above.

* * * * *